US011751820B2

(12) United States Patent
Raven

(10) Patent No.: US 11,751,820 B2
(45) Date of Patent: Sep. 12, 2023

(54) METHOD AND APPARATUS FOR PATIENT MONITORING

(71) Applicant: Michael Raven, Beverly Hills, CA (US)

(72) Inventor: Michael Raven, Beverly Hills, CA (US)

(*) Notice: Subject to any disclaimer, the term of this patent is extended or adjusted under 35 U.S.C. 154(b) by 0 days.

(21) Appl. No.: 17/196,963

(22) Filed: Mar. 9, 2021

(65) Prior Publication Data
US 2022/0287657 A1 Sep. 15, 2022

Related U.S. Application Data

(60) Provisional application No. 62/959,142, filed on Jan. 9, 2020.

(51) Int. Cl.
G08B 1/08 (2006.01)
A61B 5/00 (2006.01)
A61B 5/11 (2006.01)

(52) U.S. Cl.
CPC ............ *A61B 5/747* (2013.01); *A61B 5/1117* (2013.01); *A61B 5/6801* (2013.01); *A61B 5/7267* (2013.01); *A61B 5/7275* (2013.01)

(58) Field of Classification Search
CPC ..... A61B 5/747; A61B 5/1117; A61B 5/6801; A61B 5/7267; A61B 5/7275

USPC ..................................................... 340/539.12
See application file for complete search history.

(56) References Cited

U.S. PATENT DOCUMENTS

| 8,547,220 | B1* | 10/2013 | Dempsey | G08B 21/22 367/137 |
| 2009/0326339 | A1* | 12/2009 | Horvitz | G06Q 50/00 600/301 |
| 2016/0080486 | A1* | 3/2016 | Ram | H04L 51/046 709/205 |
| 2017/0295476 | A1* | 10/2017 | Webb | H04W 4/029 |
| 2019/0239775 | A1* | 8/2019 | Movva | A61B 5/0017 |
| 2021/0337355 | A1* | 10/2021 | Sobol | H04W 4/023 |

* cited by examiner

*Primary Examiner* — Naomi J Small
(74) *Attorney, Agent, or Firm* — Olivo IP Law Group, P.C.; John W. Olivo, Jr.

(57) ABSTRACT

The system provides a method and apparatus for patient monitoring. In one embodiment, the system comprises beacons located in the patient environment. The beacons may be part of the Medical Internet of Things (MIOT). The patient has a medical wearable that includes fall detection and non-clinical medical monitoring within a geo-fencing perimeter to assure patient safety. The caregivers wear monitoring badges that identify the location, proximity, time management and resources spent for a patient. A central hub base station in the home coordinates and collects the information from the beacons, badges, and medical wearable to deliver information (e.g., via the cloud) for the management of the patient and the caregiver.

7 Claims, 7 Drawing Sheets

METHOD AND APPARATUS FOR PATIENT MONITORING

This patent application claims priority to U.S. Provisional Patent Application 62/959,142 filed on Jan. 9, 2020, which is incorporated by reference herein in its entirety.

BACKGROUND OF THE SYSTEM

Some patients the attention of medical and/or nursing professionals. Sometimes the patient requires 24 hours monitoring to prevent problems, to prevent further injury, to prevent intentional or accidental self-harm, and to prevent the movement of a patient from a desired location. In some cases, a patient may need to be regularly turned if bedridden. In addition, patient medications must be administered at the proper time and at the proper dosage.

These actions, activities, and monitoring can be accomplished in a hospital environment where there are full time medical professionals and required monitoring equipment already in place. However, sometimes the patient needs full or part time monitoring at home or some other location away from a hospital. Some patients suffering from degenerative mental diseases, such as Alzheimer's, dementia, or degenerative physical syndromes, may need to be monitored to maintain the safety and presence of the patient. To date, such monitoring systems for home patients require physical presence of medical professionals, often several in shifts, and are expensive and do not always provide the necessary care.

SUMMARY

The system provides a method and apparatus for patient monitoring. In one embodiment, the system comprises beacons located in the patient environment. The beacons may be part of the Medical Internet of Things (MIOT). The patient has a medical wearable that includes fall detection and non-clinical medical monitoring within a geo-fencing perimeter to assure patient safety. The caregivers wear monitoring badges that identify the location, proximity, time management and resources spent for a patient. A central hub base station in the home coordinates and collects the information from the beacons, badges, and medical wearable to deliver information (e.g., via the cloud) for the management of the patient and the caregiver. Artificial intelligence (AI) is applied to the data collected to provide meaningful alerts and analysis that allows more effective handling of patients.

DETAILED DESCRIPTION OF THE SYSTEM

Figure 1:
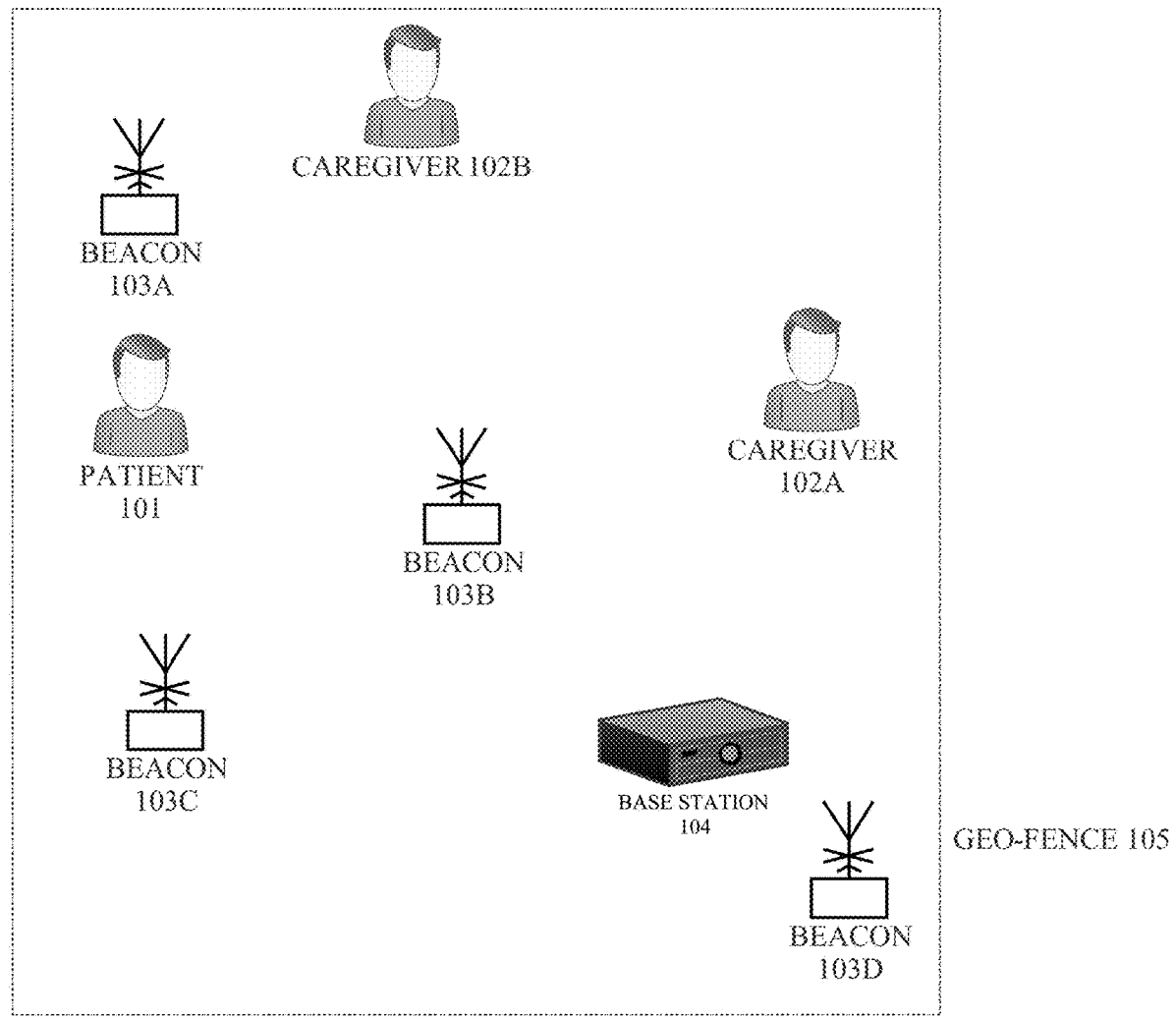
FIG. 1 illustrates an embodiment of the system in operation.

The system is a method and apparatus for patient monitoring. The system uses Beacons, Patient Wearables, Caregiver Wearables, and a Central Hub Base Station to provide highly reliable patient monitoring. The Wearables are used to provide information about the person wearing the device, including location, status (upright or fallen), certain biometrics (pulse, oxygen, etc.), activity, and the like. The Beacons are used to create a communication network of the Wearables and to define geographical boundaries to define permitted areas of movement for both patient and caregiver.

Patient Wearable

The Patient Wearable in one embodiment is a smart wearable patient/client MIOT (Medical Internet of Things) device. The devices work in conjunction with the Beacons to define a system geo-fence, a physical protected area that can be constantly electronically monitored. The Patient Wearable provides a number of functions.

In one embodiment, the Patient Wearable can perform triangulation, location, critical fall indication/physical motion/rotation (of patients), and baseline medical vitals including temperature, heart rate, and pulse/oxygen levels. The Patient Wearable works with a network of Beacons to communicate together using a custom protocol to ensure data from the patient/client Patient Wearable is secure, redundant and sent to the Base Stations for delivery to care management services in the internet cloud via AWS (Amazon Web Services).

The Patient Wearable may use industry standard sensors approved for non-clinical medical monitoring, including PulseOx Sensor Modules GY-30102 for Heart, body temperature, blood oxygen level monitoring, stress level, and XYZ Acceleration-Rotation-Motion Modules GY-521 for patient positioning (sitting, reclining, standing, moving, fall detection and location monitoring). The Patient Wearable can detect emergency events including falling, heart attack, stroke, and the like.

By monitoring location relative to the Geo-Fence, the system can determine if a patient has wandered out of a safe zone (e.g., away from home) and needs to be located and returned to the correct environment. The Patient wearable also can monitor the proximity to a caregiver to ensure that the caregiver is interacting with the patient pursuant to a schedule or care agreement.

The Patient Wearable can provide medication reminders to both the patient and the caregiver, and can include a confirmation protocol when the medication is administered.

In one embodiment the Medical Wearables are powered by Lithium-Ion Polymer Battery—3.7 v 1200 mAh which are recharged using "QI" wireless charging technology provided by the Base Station. Internal electronics are registered and certified by the FCC/CE as a Class B digital device. Internally in one embodiment the Patient Wearable contain an Espressif ESP32 microprocessor enabled with 802.11n wireless LAN-WI-FI and LE Bluetooth connectivity using the Adafruit Feather PCB package layout.

In one embodiment, the Patient Wearable may be a smart watch such as the Apple Watch, Samsung Galaxy Watch, Mobvoi, Garmin, Medical Guardian, MobileHelp, UnaliWear, OneCallAlert, and the like.

Caregiver Wearable

In one embodiment, the Caregiver Wearables are smart wearable employee/caregiver identification devices. The Caregiver Wearable should perform a number of functions including tracking the location and movement of the caregiver, uniquely identify the wearable and the caregiver, time management of the caregiver, time spent with patient, resources spent on patient, drugs administered, and other patient/caregiver related information.

In one embodiment, a proprietary algorithm is used to calculate signal strength from the Caregiver Wearables using 802.11n wireless and LE Bluetooth to perform triangulation, location, patient proximity and employee scheduling/management with proximity RFID/Digital login and logout capability. The Caregiver Wearables work with a network of Beacons to communicate together using a custom protocol to ensure data from the Caregiver Wearable is secure, redundant and sent to the Base Stations for delivery to care management services in the internet cloud via AWS (Amazon Web Services).

In one embodiment, the Caregiver Wearables are powered by a Lithium-Ion Polymer Battery—3.7 v 1200 mAh which are recharged using "QI" wireless charging technology provided by the Base Station. Internal electronics are registered and certified by the FCC/CE as a Class B digital device.

Internally the Caregiver Wearables contain an Espressif ESP32 microprocessor enabled with 802.11n wireless LAN-WI-FI and LE Bluetooth connectivity using the Adafruit Feather PCB package layout.

Also embedded within the Caregiver Wearables is an RFID chip registered to the specific badge holder that contains UUID (Universally Unique Identifier) that works/tracks with backend client care and employee management software. In one embodiment, software is loaded on power-up via internal EEPROM. Proprietary software runs automatically on power up and is written in the C programming language.

The Caregiver Wearable tracks the activities of the caregiver while the caregiver is on duty. This can include an automatic time clock for the caregiver which prevents overbilling and ensures the timeliness of scheduled care.

Beacons

The system Beacons in one embodiment are MIOT appliances that create a geo-fence to provide boundaries for a patient. The Beacons help locate a patient at all times. In one embodiment, the geo-fence created by the Beacons works using WiFi and Low Energy Bluetooth technology to triangulate the location of both the patient (having the Patient Wearable) and one or more caregivers (having the Caregiver Wearable). The Beacons transmit the location and positioning information to the Base Station for analysis. Using the same communication technology, the system transmits and relays patient medical data from the Patient Wearable to the Base Station.

In one embodiment, the Beacons are powered by UL certified external 5-volt USB power adapters and internal electronics are registered and certified by the FCC/CE as a Class B digital device.

Internally the Beacons contain a BMC2835 1 GHZ ARM11 microprocessor enabled with 802.11n wireless LAN-WI-FI and LE Bluetooth connectivity using the Raspberry PI Zero/W PCB package layout.

Software is loaded on power-up via Micro SD Card. Base operating system is based on a Debian Linux derivative. Proprietary software runs automatically on power up and is written in C and Python programming languages.

In one embodiment, user feedback for each Beacon is provided by, for example, an Adafruit Neopixel 12 light ring. This light ring provides a visual indication of standard operation and/or any errors.

The Beacons can function as night lights. In one embodiment, the Beacons can also be used as two-way communication devices including speakers and microphones.

In one embodiment, the Wearables can use their own GPS systems to track the patient and caregivers and can be used with or without the Beacons as desired.

In one embodiment, the system includes a spectrometer in an air filtration system to detect airborne particulates, viruses, and bacteria that could have an impact on the patient and provides detection data to the system.

Base Station

In one embodiment the Base Station is a local IOT (Internet of Things) hub device that collects and monitors data from Caregiver Wearables and Patient Wearables through a network of Beacons. This device is the central management device for the geo-fence (a physical protected area that can be constantly electronically monitored) home environment. In one embodiment a proprietary algorithm is used to calculate signal strength to the Base Station using 802.11n wireless and LE Bluetooth to perform triangulation, location, patient proximity and employee scheduling/management with proximity RFID/Digital login and logout capability. The Base Station works with a network of Beacons to communicate together using a custom protocol to ensure data from the Caregiver Wearable and Patient Wearable is secure, redundant and sent to care management services in the internet cloud via AWS (Amazon Web Services).

A Base Station is powered by UL certified external 5-volt USB power adapter and internal electronics are registered and certified by the FCC/CE as a Class B digital device. Using "QI" wireless charging technology the Base Station provides power charging for Caregiver Wearables and Patient Wearables.

In one embodiment, internally the Base Station contains.
SOC: Broadcom BCM2837B0, Cortex-A53 (ARMv8) 64-bit SoC
CPU: 1.4 GHz 64-bit quad-core ARM Cortex-A53 CPU
RAM: 1 GB LPDDR2 SDRAM
WIFI: Dual-band 802.11ac wireless LAN (2.4 GHz and 5 GHz) and Bluetooth 4.2
Ethernet: Gigabit Ethernet over USB 2.0 (max 300 Mbps). Power-over-Ethernet support (with separate PoE HAT). Improved PXE network and USB mass-storage booting.
Thermal management: Yes
Video: Yes—VideoCore IV 3D. Full-size HDMI
Audio: Yes
USB 2.0 (or higher): 4 ports
GPIO: 40-pin
Power: 5V/2.5 A DC power input
Operating system support: Linux and Unix Also embedded within the Base Station, is a charging system for both the Caregiver Wearables and Patient Wearables using "QI" wireless charging technology Software may be loaded on power-up via Micro SD Card. In one embodiment, the Base operating system is based on a Debian Linux derivative. Proprietary software runs automatically on power up and is written in C and Python programming languages.

In one embodiment, user feedback for the Base Station is provided by, for example, an Adafruit Neopixel 12 light ring. This light ring provides a visual indication of standard operation and/or any errors.

System

FIG. 1 illustrates an embodiment of the system in operation. The patient 101 wears a Patient Wearable that communicates with Beacons 103A-103D and Base Station 104. The Beacons define a geo-fence 105 that establishes a boundary for the patient 101. Caregivers 102A and 102B are attending the patient within the geo-fence 105 and each wear a Caregiver Wearable that communicates with the Beacons and the Base Station. The Beacons 103A-103D communicate with the Base Station 104, Patient Wearable and Caregiver Wearable. An AI integration detects patterns for potential negative health events and sends appropriate alerts for Caregivers and/or other medical professionals to investigate.

The system tracks the location and status of the patient, detecting falls, lack of movement, changes in vitals, movement outside the geo-fence perimeter and the like. The system also tracks the location of the one or more caregivers. If the caregiver is not spending enough time within a threshold distance from the patient during a shift, the system will send a notification to the caregiver and to the system so that remedial action may be taken. If the caregiver is not responsive to the notification and/or is not attending the patient, a replacement caregiver can be automatically dispatched to rectify the situation. If there is an emergency with the patient, the system can alert the nearest caregiver so that emergency procedures can be implemented more quickly.

Figure 2:
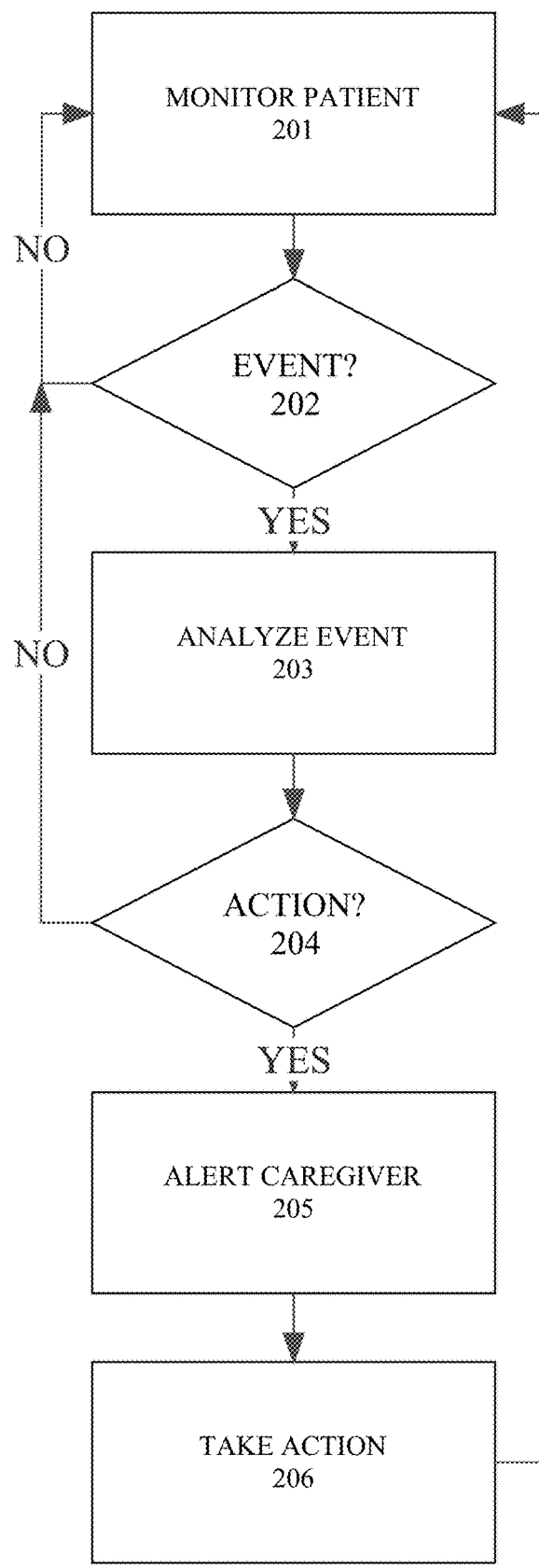
FIG. 2 is a flow diagram illustrating the operation of the system in an embodiment.

FIG. 2 is a flow diagram of the operation of the system in an embodiment. At step 201 the system monitors the patient. This is accomplished be the Base Station receiving biometric, position, accelerometer, location, and other information from the Patient Wearable and the Beacons. At step 202 it is determined if some event has occurred. If not, the system returns to step 201 and continues monitoring the patient.

If there is an event at step 202, the system analyses the event at step 203. This analysis includes characterizing the event as medical based, movement based, location based, and the like. At decision block 204 it is determined if the event requires action. For example, the even could be an accelerometer reading that indicates a fall. The event could represent a change in vital signs, or movement outside of a Geo-Fence area. If not, the system returns to step 201 and continues monitoring the patient.

If the even requires action at decision block 204, the system alerts a caregiver at step 205. At step 206 the caregiver takes the appropriate action, and the system returns to monitoring the patient at step 201.

Figure 3:
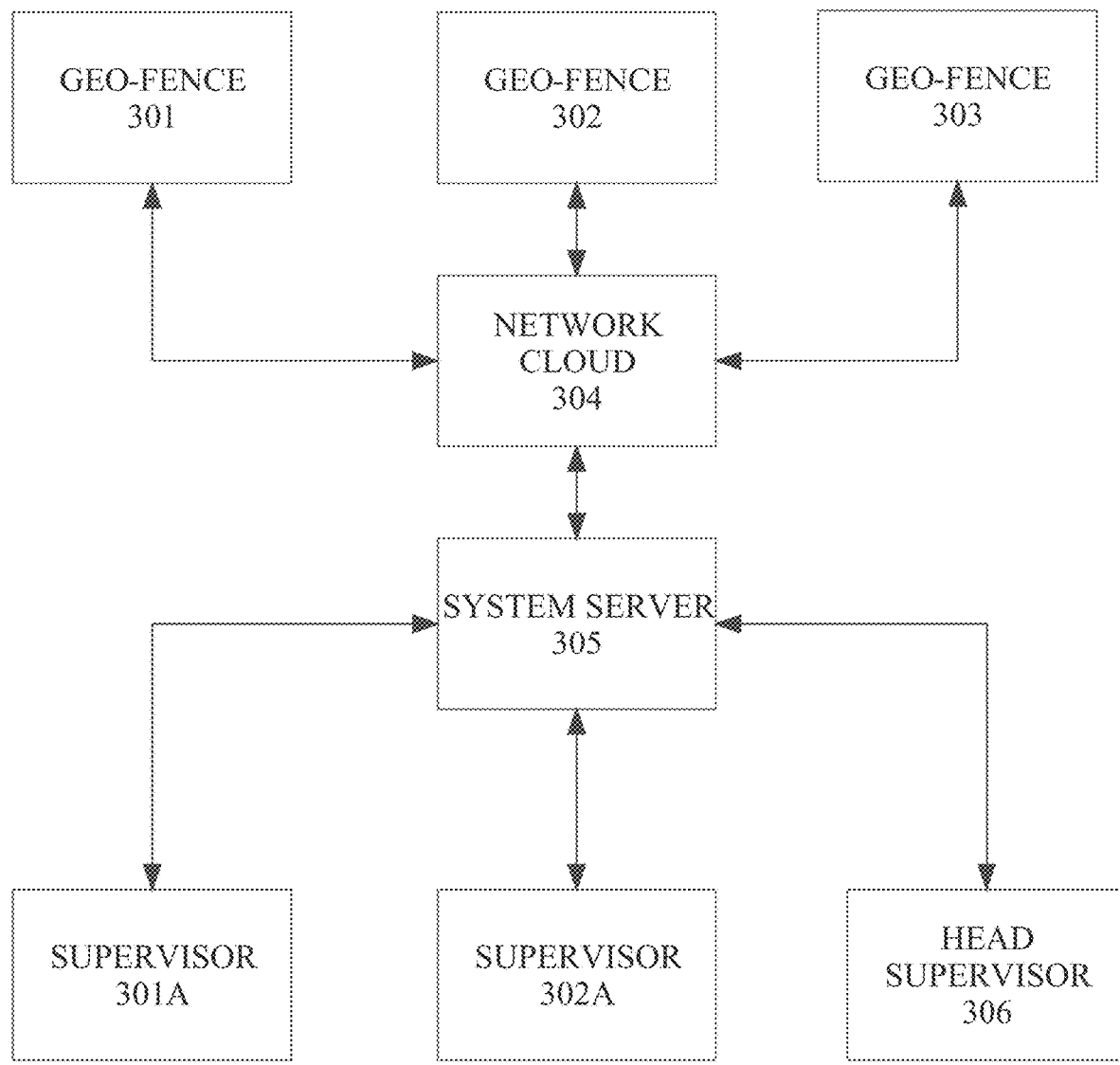
FIG. 3 illustrates an example topography in an embodiment of the system.

FIG. 3 illustrates an embodiment of a topography of the system. Geo-Fence locations 301, 302, and 303 each comprise at least one patient with a Patient Wearable, at least one caregiver with a Caregiver Wearable, at least one Base Station, and one or more Beacons used to define a Geo-Fence around the patient. (In an embodiment where no Beacons are used, the system can define a geo-fence by defining a distance from a specific geolocation, forming a circular Geo-Fence). In other embodiments where no Beacons are used, GPS coordinates can be defined in any geographical shape as desired to define the Geo-Fence.

The Base Station of each Geo-Fence communicates to a System Server 305 via Network Cloud 304 (e.g., the Internet). The System Server 305 receives data from the wearables via the Base Stations at each location. The System Server then applies analysis, AI, and other review to determine actions and responses that may be necessary.

The System Server 305 can be monitored by Caregiver supervisors to add an additional element of service and protection to the patients. In one embodiment, a caregiver supervisor can only access data from a Geo-Fence associated with the caregivers under that supervisor. For example, Supervisor 301A can only access data from Geo-Fence 301. Similarly, Supervisor 302A can only access data from Geo-Fence 302. A Head Supervisor 306 has permission to access data from all Geo-Fence locations. These levels of permission help prevent unauthorized access of data.

Figure 4:
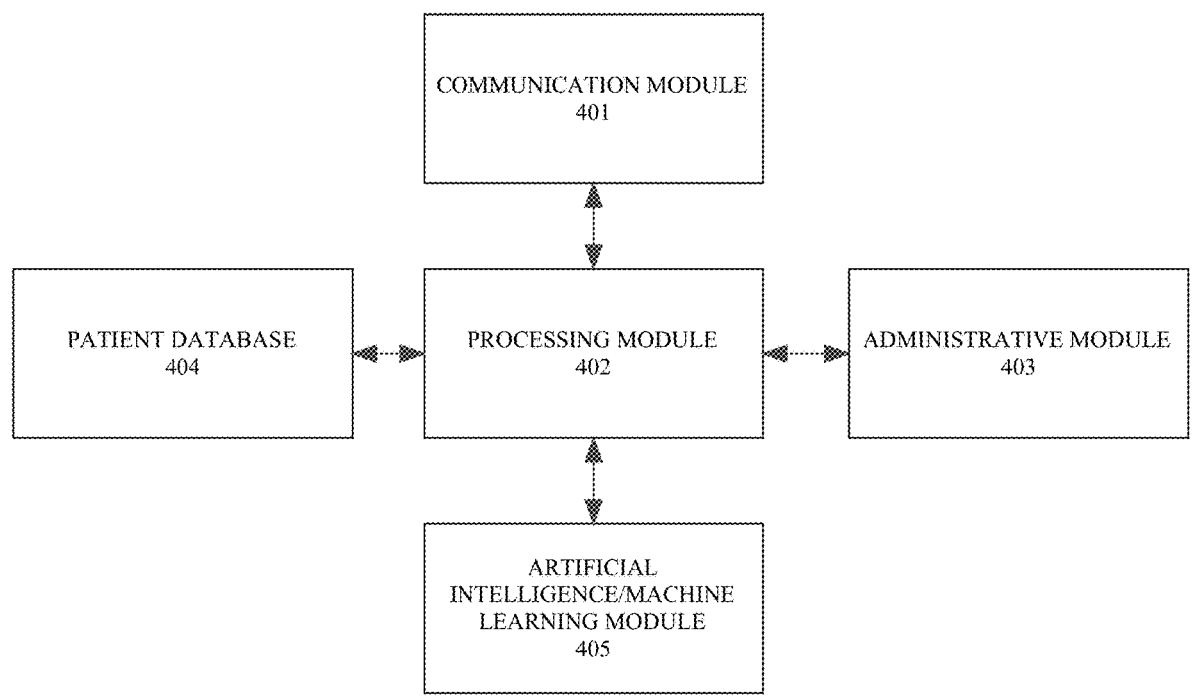
FIG. 4 illustrates a System Server in an embodiment of the system.

FIG. 4 illustrates the System Server in an embodiment of the system. The System Server 305 comprises a Communication Module 401 to send and receive data to the Base Station 104. In one embodiment, the Communication Module and communicate directly with the Beacons, Patient Wearable, and/or the Caregiver Wearable. The Communication Module 401 is coupled to Processing Module 402 which performs operations and programs on the data.

Processing Module 402 is coupled to Patent Database Module 404. Patient Database Module 404 stores all patient information, permission levels, care schedules, medications and medication schedules, baseline information and historical information for patients and triggers that can be based on patient biometrics detected by the Patient Wearables. The Administrative Module 403 includes a database and processing for the Caregivers and Caregiver Supervisors. The Administrative Module 403 can handle the timekeeping of the Caregivers and related staff, payroll and other financial functions, and monitor licensing and permits required for medical staff.

The Artificial Intelligence/Machine Learning Module 405 (AI Module) applies AI and machine learning to patient and caregiver data to identify events, rank the events in terms of importance, predict possible patient problems requiring attention, and use patient baseline and medical data to catch problems before they happen.

The AI Module 405 receives live feeds of data from all wearables, beacons, and base stations. The AI Module 405 can analyze the data and compare it to scheduled caregiver tasks and historical data to determine what activities are occurring with the patient and caregivers. For example, the AI Module can determine if both the patient and caregiver are located in a bathroom and, based on the time, determine if the patient is being bathed or if the patient is being assisted to use a toilet. Similarly, the AI can determine based on prior locations of the caregiver and interactions with the patient, if the patient is being fed, being administered medication, and the like. Unscheduled interaction between a caregiver and a patient may be in response to a call for assistance from the patient.

The AI Module 405 can also monitor the biometrics of a patient and compare it to a baseline to determine if extra attention is required. The same analysis can spot declining metrics of a patient and provide alerts to a medical professional for intervention and prevention.

Figure 5:
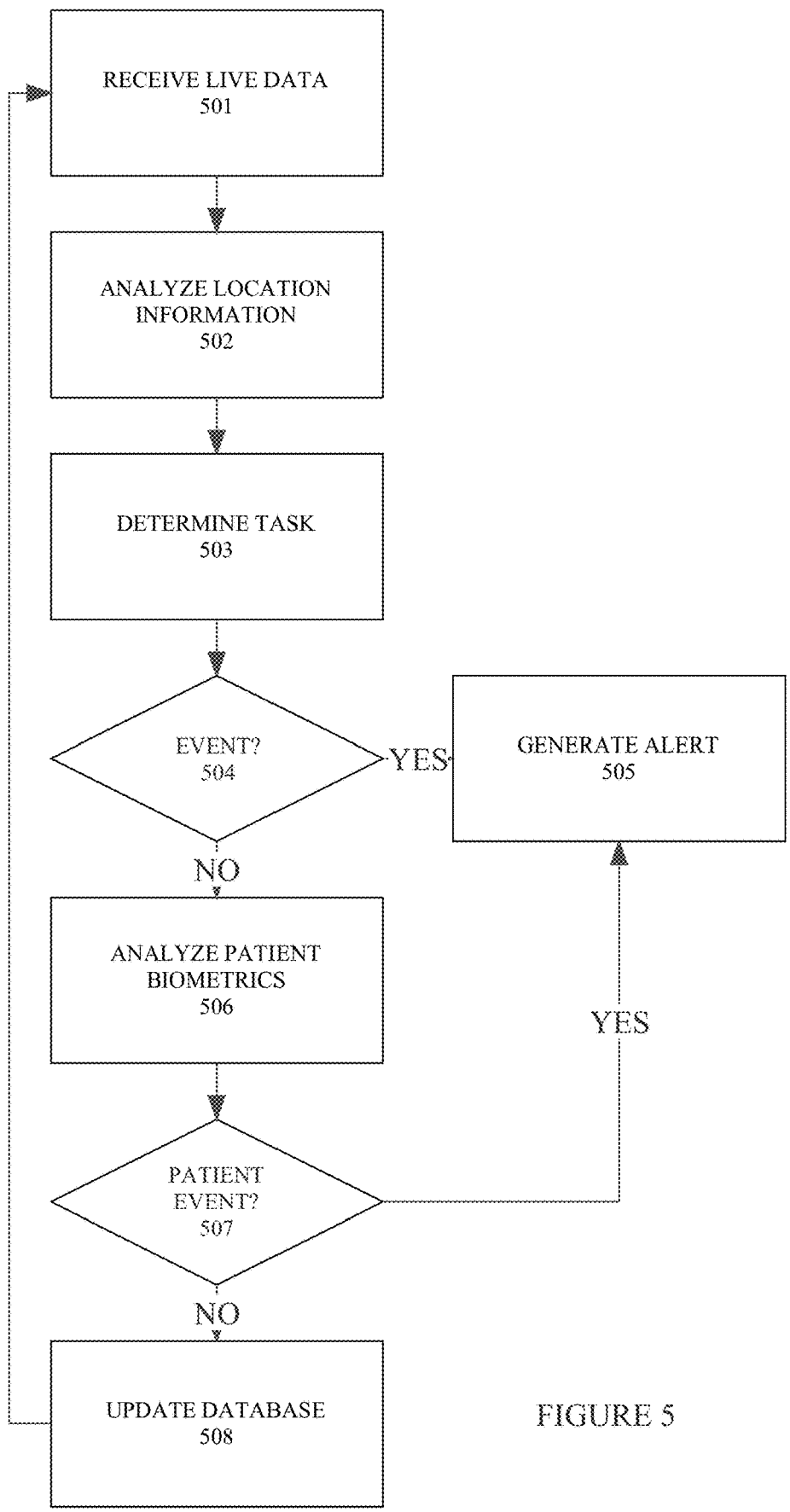
FIG. 5 is a flow diagram illustrating the operation of the AI Module in an embodiment of the system.

FIG. 5 is a flow diagram illustrating the operation of the AI Module in an embodiment of the system. At step 501 the module receives data streams from all of the wearables, beacons, and base units in the field. These units include identifiers so that the AI can place them in an appropriate Geo-Fence location.

At step 502, the AI Module 405 analyzes the data to track each wearable and to determine proximity of a patient and one or more caregivers. At step 503, the module uses near term historical location information, as well as caregiver schedules and historical data, to determine a procedure or task being performed with or on the patient by the caregiver. For example, if the caregiver has just been near a medication supply area, and then approaches a patient, the module may infer that patient medication is about to be administered. The module can compare the current time to a scheduled time for medication, along with the timing of prior administration of medication, to make sure that the timing of the medication is appropriate. The module has a list of patient medication with a dosage schedule, interactions, and other modalities to make sure that the current task is appropriate. In one embodiment, the caregiver provides an update of the type and dosage of medication provided, allowing the module to update the history of the medication.

The module uses machine learning and AI to determine at all times if some action is taking place, whether the action is scheduled, and if an event should be triggered. Such activities can be eating, sleeping, exercise, bathing, examination, and the like. At decision block 504 the AI Module 405 determines if the detected action should trigger an event. If so, the system generates an alert at step 505.

If the activities does not rise to the level of an event, the system proceeds to step 506 where the module analyzes the patient biometrics. In this step, the AI Module 405 can analyze all the available patient biometric information and determine if the patient is experiencing a medical issue that requires attention. This determination can be based on current data that shows metrics outside of expected ranges, such as high temperature, low oxygen, a fall, low pulse, and the like. The determination can also be based on historical data and/or patient baseline data. For example, if blood oxygen is declining over time, but has not yet reached dangerous levels, the system can trigger an event so that a caregiver or medical professional can intervene before the condition deteriorates further. Other indicators can be loss of weight, decreased activity, or other metrics that show risk or decline.

The system uses historical data from the current patient and Geo-Fence location, as well as data from all other patients using the system. For each event, the AI will look back at historical data prior to the event to identify commonalities and metric changes that are consistent prior to the same event over time. The system can then look for these common metrics to predict possible events before they happen, and to alert caregivers to look for possible signs related to an event. As the AI learns and ingests data, the ability to improve its performance is enhanced.

At decision block 507 it is determined if the patient status is such that an event is triggered. If so, an alert is generated at step 505. If not, the patient history database is updated at step 508 and the system returns to step 501.

Figure 6:
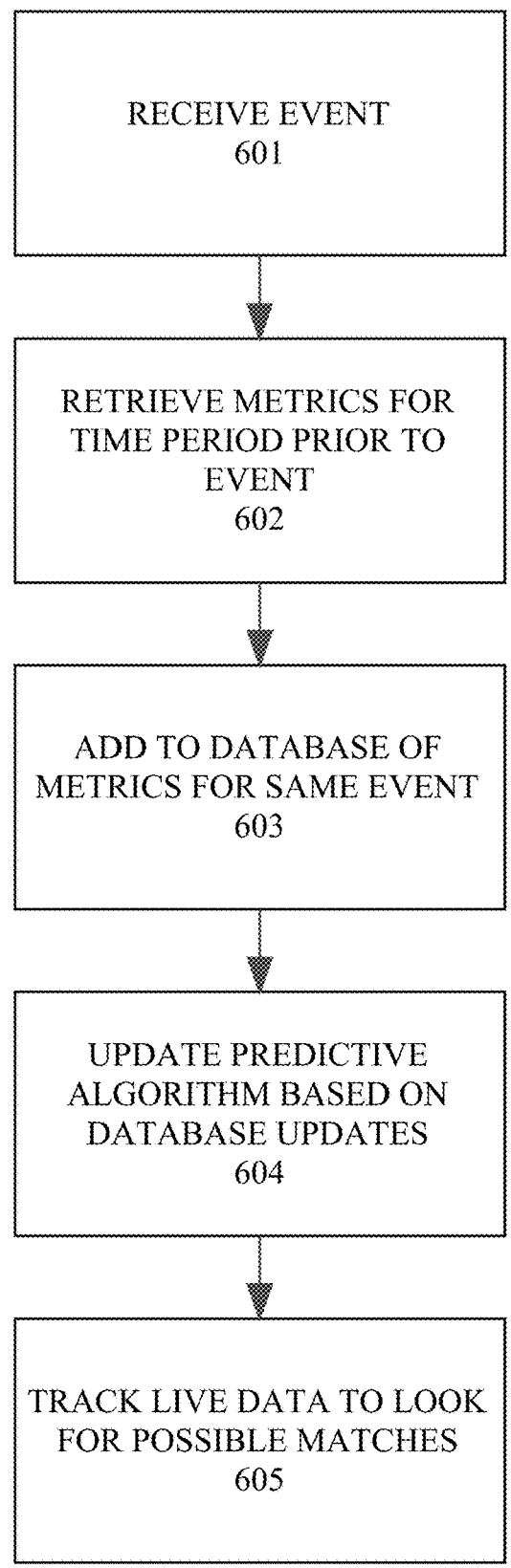
FIG. 6 is a flow diagram illustrating training of the AI in an embodiment of the system.

FIG. 6 is a flow diagram of the learning processes of the AI of the system. At step 601 the AI receives an event. At step 602 the AI tracks metrics for some time period prior to the event. This could be hours, days, or weeks, depending on the event. The metrics could include biometric data, location data; caregiver interaction data, medication data (including changes in medication and dosage); diet, sleep, and the like.

At step 603 the system adds the metrics for the patient to a database of metrics for the same event from any patient who experienced the event. The data can be used to update histograms, relational databases, and the like, so that it can be used to support predictive tools. At step 604 the system can update its predictive algorithm based on the database updates. In the future, when monitoring metrics for a patient at step 605, if the metrics begin to match up with the pre-event metrics stored in the database, an alert can be provided to caregivers.

Example Computer System

Figure 7:
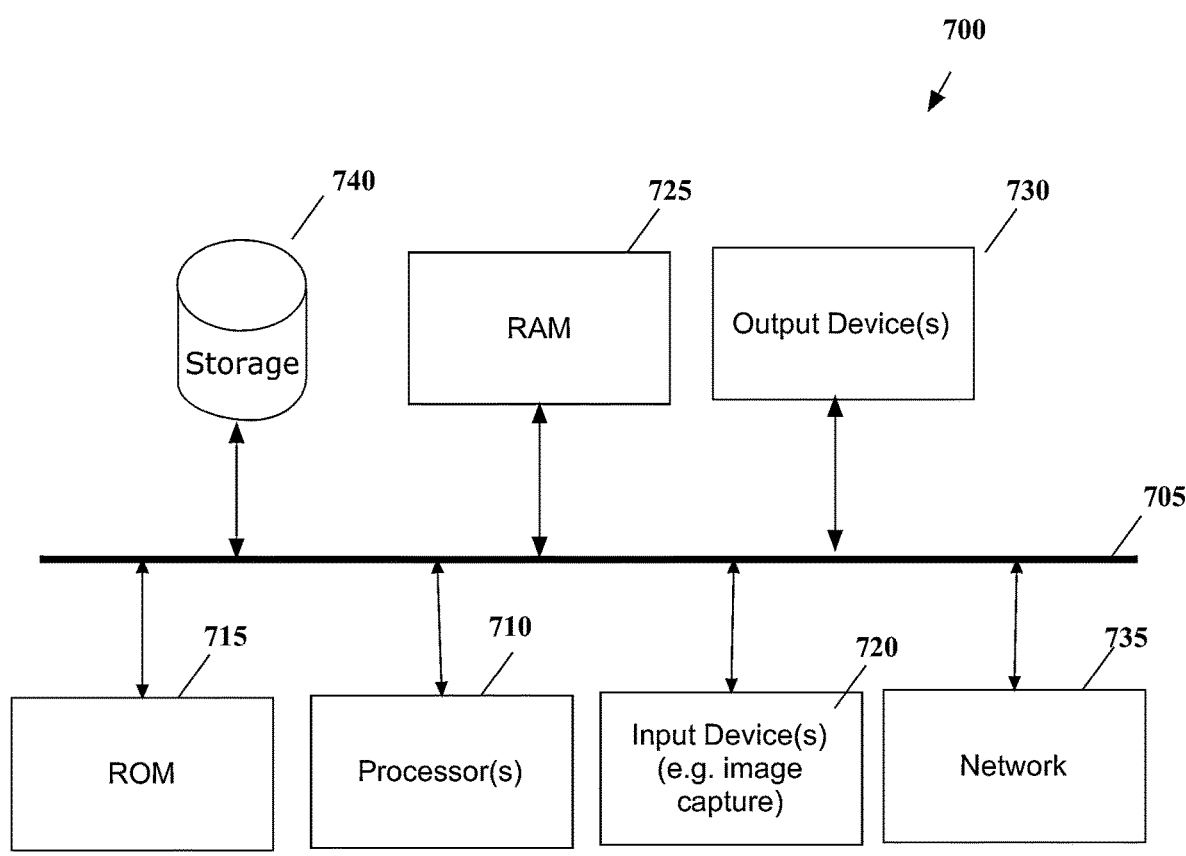
FIG. 7 is an example computer system in an embodiment of the system.

FIG. 7 illustrates an exemplary a system 700 that may implement the system. The electronic system 700 of some embodiments may be a mobile apparatus. The electronic system includes various types of machine-readable media and interfaces. The electronic system includes a bus 705, processor(s) 710, read only memory (ROM) 715, input device(s) 720, random access memory (RAM) 725, output device(s) 730, a network component 735, and a permanent storage device 740.

The bus 705 communicatively connects the internal devices and/or components of the electronic system. For instance, the bus 705 communicatively connects the processor(s) 710 with the ROM 715, the RAM 725, and the permanent storage 740. The processor(s) 710 retrieve instructions from the memory units to execute processes of the invention.

The processor(s) 710 may be implemented with one or more general-purpose and/or special-purpose processors. Examples include microprocessors, microcontrollers, DSP processors, and other circuitry that can execute software. Alternatively, or in addition to the one or more general-purpose and/or special-purpose processors, the processor may be implemented with dedicated hardware such as, by way of example, one or more FPGAs (Field Programmable Gate Array), PLDs (Programmable Logic Device), controllers, state machines, gated logic, discrete hardware components, or any other suitable circuitry, or any combination of circuits.

Many of the above-described features and applications are implemented as software processes of a computer programming product. The processes are specified as a set of instructions recorded on a machine-readable storage medium (also referred to as machine readable medium). When these instructions are executed by one or more of the processor(s) 710, they cause the processor(s) 710 to perform the actions indicated in the instructions.

Furthermore, software shall be construed broadly to mean instructions, data, or any combination thereof, whether referred to as software, firmware, middleware, microcode, hardware description language, or otherwise. The software may be stored or transmitted over as one or more instructions or code on a machine-readable medium. Machine-readable media include both computer storage media and communication media including any medium that facilitates transfer of a computer program from one place to another. A storage medium may be any available medium that can be accessed by the processor(s) 710. By way of example, and not limitation, such machine-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a processor. Also, any connection is properly termed a machine-readable medium. For example, if the software is transmitted from a website, server, or other remote source using a coaxial cable, fiber optic cable, twisted pair, digital subscriber line (DSL), or wireless technologies such as infrared (IR), radio, and microwave, then the coaxial cable, fiber optic cable, twisted pair, DSL, or wireless technologies such as infrared, radio, and microwave are included in the definition of medium. Disk and disc, as used herein, include compact disc (CD), laser disc, optical disc, digital versatile disc (DVD), floppy disk, and Blu-ray® disc where disks usually reproduce data magnetically, while discs reproduce data optically with lasers. Thus, in some aspects machine-readable media may comprise non-transitory machine-readable media (e.g., tangible media). In addition, for other aspects machine-readable media may comprise transitory machine-readable media (e.g., a signal). Combinations of the above should also be included within the scope of machine-readable media.

Also, in some embodiments, multiple software inventions can be implemented as sub-parts of a larger program while remaining distinct software inventions. In some embodiments, multiple software inventions can also be implemented as separate programs. Any combination of separate programs that together implement a software invention described here is within the scope of the invention. In some embodiments, the software programs, when installed to operate on one or more electronic systems 700, define one or more specific machine implementations that execute and perform the operations of the software programs.

The ROM 715 stores static instructions needed by the processor(s) 710 and other components of the electronic system. The ROM may store the instructions necessary for the processor(s) 710 to execute the processes provided by the system. The permanent storage 740 is a non-volatile memory that stores instructions and data when the electronic system 700 is on or off. The permanent storage 740 is a read/write memory device, such as a hard disk or a flash drive. Storage media may be any available media that can be accessed by a computer. By way of example, the ROM could also be EEPROM, CD-ROM or other optical disk storage, magnetic disk storage or other magnetic storage devices, or any other medium that can be used to carry or store desired program code in the form of instructions or data structures and that can be accessed by a computer.

The RAM 725 is a volatile read/write memory. The RAM 725 stores instructions needed by the processor(s) 710 at runtime, the RAM 725 may also store the real-time video or still images acquired by the system. The bus 705 also connects input and output devices 720 and 730. The input devices enable the user to communicate information and select commands to the electronic system. The input devices 720 may be a keypad, image capture apparatus, or a touch screen display capable of receiving touch interactions. The output device(s) 730 display images generated by the electronic system. The output devices may include printers or display devices such as monitors.

The bus 705 also couples the electronic system to a network 735. The electronic system may be part of a local area network (LAN), a wide area network (WAN), the Internet, or an Intranet by using a network interface. The electronic system may also be a mobile apparatus that is connected to a mobile data network supplied by a wireless carrier. Such networks may include 3G, HSPA, EVDO, and/or LTE.

It is understood that the specific order or hierarchy of steps in the processes disclosed is an illustration of exemplary approaches. Based upon design preferences, it is understood that the specific order or hierarchy of steps in the processes may be rearranged. Further, some steps may be combined or omitted. The accompanying method claims present elements of the various steps in a sample order, and are not meant to be limited to the specific order or hierarchy presented.

The various aspects of this disclosure are provided to enable one of ordinary skill in the art to practice the present invention. Various modifications to exemplary embodiments presented throughout this disclosure will be readily apparent to those skilled in the art, and the concepts disclosed herein may be extended to other apparatuses, devices, or processes. Thus, the claims are not intended to be limited to the various aspects of this disclosure, but are to be accorded the full scope consistent with the language of the claims. All structural and functional equivalents to the various components of the exemplary embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 18(f) unless the element is expressly recited using the phrase "means for" or, in the case of a method claim, the element is recited using the phrase "step for."

Thus, an improved patient monitoring system has been described.

What is claimed is:

1. A method of monitoring a patient comprising:
defining a boundary of said patient using a plurality of beacons, wherein said plurality of beacons detect patient location relative to said plurality of beacons using data from a patient wearable worn by said patient;
alert said patient and a caregiver when said patient's location is near said boundary via speakers and allow for said patient and said caregiver to respond via a microphone;
securely communicate with each of said plurality of beacons, said patient wearable, and a caregiver wearable worn by said caregiver;
securely communicate with at least one spectrometer placed in an air filtration system that detects airborne particulates, viruses, and bacteria; and
send, to a system that performs machine learning analysis, data regarding previous patient movements to determine patient behavioral patterns; and
wherein said method further comprises securely transmitting location information from said patient wearable and said caregiver wearable to said system that performs machine-learning analysis for predicting and alerting said caregiver when said patient travels outside of said boundary:
including at least one caregiver within said boundary wearing said caregiver wearable that tracks the location of said caregiver relative to said patient and to said plurality of beacons;
alerting said patient and said caregiver with medication reminders and protocols to confirm administration of said medication;
detecting said patient's physical orientation and alerting said caregiver when said patient's orientation changes; and
determining patterns of said patient's diet and behavior based on artificial intelligence (AI) analysis of said patient's dietary and behavioral data.

2. The method of claim 1 further including at least one base station for communicating data to and from said plurality of beacons, patent wearable, and caregiver wearable and wherein said at least one base station detects the battery life of said plurality of beacons, said patient wearable, and said caregiver wearable and provide at least one charging platform for each.

3. The method of claim 2 further including a system server coupled to said at least one base station for analyzing said data using artificial intelligence (AI).

4. The method of claim 3 wherein said patient wearable monitors heart rate, temperature, and pulse/oxygen levels of said patient.

5. The method of claim 4 wherein said AI uses said biometric data to predict a patient event, wherein said patient event requires intervention.

6. The method of claim 5 wherein said caregiver is notified when said patient event is predicted.

7. The method of claim 6 wherein a learning database is updated with patient data when said patient event occurs.

\* \* \* \* \*